United States Patent
Mehta et al.

(10) Patent No.: US 11,628,147 B2
(45) Date of Patent: Apr. 18, 2023

(54) VITAMIN K2 COMPOSITIONS FOR THE TREATMENT OF DRUG INDUCED NEUROPATHY

(71) Applicant: SYNERGIA LIFE SCIENCES PVT. LTD., Mumbai (IN)

(72) Inventors: Dilip Mehta, Mumbai (IN); Ashok Vaidya, Mumbai (IN); Rama Vaidya, Mumbai (IN); Yogesh Dound, Mumbai (IN); Anselm De Souza, Mumbai (IN)

(73) Assignee: SYNERGIA LIFE SCIENCES PVT. LTD., Mumbai (IN)

( * ) Notice: Subject to any disclaimer, the term of this patent is extended or adjusted under 35 U.S.C. 154(b) by 0 days.

(21) Appl. No.: 16/954,949

(22) PCT Filed: Dec. 13, 2018

(86) PCT No.: PCT/IB2018/060038
§ 371 (c)(1),
(2) Date: Jun. 17, 2020

(87) PCT Pub. No.: WO2019/123144
PCT Pub. Date: Jun. 27, 2019

(65) Prior Publication Data
US 2020/0330401 A1    Oct. 22, 2020

(30) Foreign Application Priority Data
Dec. 19, 2017 (IN) .............................. 201721045728

(51) Int. Cl.
| | | |
|---|---|---|
| *A61K 31/122* | (2006.01) | |
| *A61P 25/02* | (2006.01) | |
| *A61K 31/4375* | (2006.01) | |
| *A61K 31/454* | (2006.01) | |
| *A61K 31/573* | (2006.01) | |
| *A61K 31/675* | (2006.01) | |
| *A61K 31/69* | (2006.01) | |
| *A61K 38/05* | (2006.01) | |

(52) U.S. Cl.
CPC ........ *A61K 31/122* (2013.01); *A61K 31/4375* (2013.01); *A61K 31/454* (2013.01); *A61K 31/573* (2013.01); *A61K 31/675* (2013.01); *A61K 31/69* (2013.01); *A61K 38/05* (2013.01); *A61P 25/02* (2018.01)

(58) Field of Classification Search
CPC .............................. A61K 31/122; A61P 25/02
See application file for complete search history.

(56) References Cited

U.S. PATENT DOCUMENTS

| | | |
|---|---|---|
| 2010/0130618 A1 | 5/2010 | Vaidya et al. |
| 2014/0134172 A1 | 5/2014 | Gu et al. |
| 2015/0126763 A1 | 5/2015 | Mehta et al. |
| 2015/0148296 A1 | 5/2015 | Kawabata et al. |

OTHER PUBLICATIONS

Ria et al. Int. J. Clin. Exp. Med., 2013, vol. 6, No. 1, pp. 30-38 (Year: 2013).*
International Search Report and Written Opinion for PCT/IB2018/060038, dated Apr. 30, 2019.
Addington, J. et al., Chemotherapy-induced peripheral neuropathy: an update on the current understanding. F1000 Research, Jun. 22, 2016, 5(F1000 Faculty Rev):1466.
Ben-Horin, Idan, et al., Acupuncture and Reflexology for Chemotherapy-Induced Peripheral Neuropathy in Breast Cancer. Integrative Cancer Therapies. Dec. 23, 2016, vol. 16(3) 258-262.
Bruna, J., et. al. Efficacy of a Novel Sigma-1 Receptor Antagonist for Oxaliplatin-In Nduced Neuropathy: A Randomized, Double-Blind, Placebo-Controlled Phase IIa Clinical Trial. Neurotherapeutics, Sep. 18, 2017 (published online); 15: 178.
Grammatico S, et al., Managing treatment-related peripheral neuropathy in patients with multiple myeloma. Blood and Lymphatic Cancer: Targets and Therapy Jun. 29, 2016:6 37-47.
Lakhan Se, et al., Toxin-A for Painful Diabetic Neuropathy: A Meta-Analysis. Pain Med., Sep. 2015; 16(9):1773-80.
Majithia, N. et al., New Practical Approaches to Chemotherapy-Induced Neuropathic Pain: Prevention, Assessment, and Treatment. Oncology (Williston Park). Nov. 2016, 15;30(11):1020-9.
Manuel, Diezi, et al., Toxic and drug-induced peripheral neuropathies: updates on causes, mechanisms and management. CurrOpin Neurol., Oct. 2013;26(5):481-8.
Mohty, Bilal, et al., Peripheral neuropathy and new treatments for multiple myeloma: background and practical recommendations. Haematologica, Feb. 2010 ( 95): 311-319.
Wewers, Me, et al., A critical review of visual analogue scales in the measurement of clinical phenomena. Res. Nur. Health, Aug. 1990; 13(4):227-36.
Diezi, et al., Toxic and drug-induced peripheral neuropathies: updates on causes, mechanisms and management, Co-Neurology, vol. 26, No. 5, Oct. 2013, pp. 481-488.

* cited by examiner

*Primary Examiner* — James D. Anderson
(74) *Attorney, Agent, or Firm* — Bryan D. Zerhusen; Nicholas R. Herrel; Cantor Colburn LLP

(57) ABSTRACT

The present invention provides the use of vitamin K2 compositions for the treatment of drug-induced neuropathy. More particularly it is related to the use of vitamin K2-7 compositions for the treatment of drug-induced peripheral neuropathy caused by the drugs used for the treatment of multiple myeloma.

13 Claims, 1 Drawing Sheet

Schematic 1. Visual Analog Scale with gradations
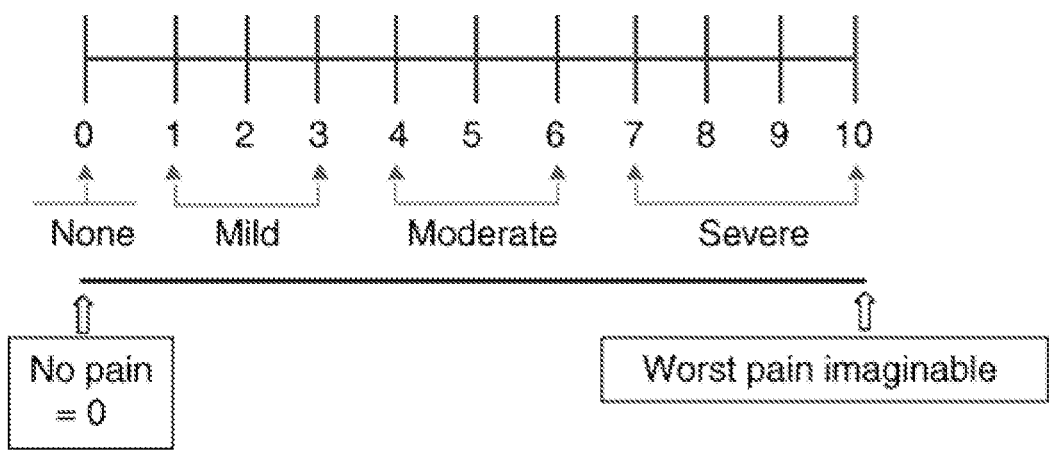

VITAMIN K2 COMPOSITIONS FOR THE TREATMENT OF DRUG INDUCED NEUROPATHY

RELATED APPLICATIONS

This application is a National Stage Application of International Application No. PCT/IB2018/060038, filed 13 Dec. 2018 and published as WO 2019/123144 A1 on 27 Jun. 2019, which claims priority and the benefit of Indian Provisional Patent Application No. 201721045728 filed on 19 Dec. 2017, each of which is incorporated herein by reference in its entirety.

FIELD OF THE INVENTION

The present invention is related to the use of vitamin K2 and compositions containing the same for the treatment of drug-induced neuropathy. More particularly, the present disclosure relates to the use of vitamin K2-7 and compositions containing the same for the treatment of drug-induced peripheral neuropathy caused by drugs used for the treatment of multiple myeloma.

BACKGROUND OF THE INVENTION

Peripheral neuropathy refers to a broad range of disorders affecting the peripheral nerves. A wide range of factors can lead to peripheral neuropathy, such as Type II Diabetes Mellitus, alcohol abuse, paraneoplastic syndromes or toxins, vitamin B12 deficiency, etc. The peripheral nervous system consists of motor nerves, sensory nerves, and autonomic nerves. The severity of the condition depends on the factors responsible and the duration of the condition. Sensory neuropathy symptoms are distal dysesthesias which is pain and numbness that begins with the distal portions of the nerves. It also begins with a loss of temperature and vibratory perception in the toes and feet to begin with. Motor neuropathy symptoms are characterized by weakness. Muscle tone is slowly lost and turns flaccid. Reflexes are also slowly lost. Autonomic neuropathy dysfunction is reflected by orthostatic hypotension.

Drug-induced peripheral neuropathy refers to a more specific form of peripheral neuropathy caused by the administration of certain drugs, which (i) are toxic when administered over extended periods of time, (ii) can lead to loss of movement and sensation along with experiences of numbness, tingling, burning in hands and feet, as well as (iii) muscle weakness. Drug-induced peripheral neuropathy (DIPN) can begin after few weeks or months after the treatment is initiated. DIPN leads to discomfort and pain but is not fatal. DIPN can be treated by discontinuing the drug that caused the condition, lowering the dose of the drug that caused the condition, and/or administering pain relievers. Treatment of drug-induced peripheral neuropathy can take few weeks or months to be effective depending upon the severity of the condition. Also, the damage caused by drug-induced peripheral neuropathy could be reversible or permanent. The symptoms of drug-induced neuropathy are muscle weakness, claudication (experience of loss in sensation beginning in the hands and feet, spreading towards the body), and numbness, tingling, or abnormal sensations in the hands and/or feet. Constant tingling and numbness may occur in the area surrounding the affected nerves. The magnitude of severity can vary from patient to patient. The loss of sensation could be partially reversible or permanent due to permanent nerve damage.

A wide range of drugs are reported to cause DIPN depending on their toxicity to the body. The classes of drugs and specific examples are as follows: (1) drugs for the treatment of autoimmune diseases, such as etanercept, infliximab, leflunomide, azathioprine, cyclophosphamide, cyclosporine, mycophenolate, and methotrexate; (2) anti-infectives, such as chloroquine, isoniazid, metronidazole, nitrofurantoin, and thalidomide; (3) anti-HIV drugs, such as didanosine, stavudine, and zalcitabine; and (4) anti-cancer drugs, such as cisplatin, vincristine, and paclitaxel. For instance, combination of vinca alkaloids and cisplatin is reportedly more toxic. Similarly, a combination of paclitaxel and cisplatine or carboplatin is highly toxic. Further examples of classes of drugs and specific examples include: (5) drugs for the treatment of alcohol abuse, such as disulfiram; (6) cardiovascular drugs, such as statins especially simvastatin, pravastatin, fluvastatin, and amiodarone; and (7) drugs for the treatment of multiple myeloma, e.g. bortezomib and thalidomide. Combination of bortezomib and thalidomide has been recommended for refractory multiple myeloma; however, the combination is reportedly more toxic than a single drug. Similarly, epothilones are used in the treatment of advanced breast cancer. Ixabepilone used to treat refractory breast cancer is known to cause severe peripheral neuropathy. In some cases, vitamin B12 administration is known to ameliorate symptoms. Furthermore, (8) biological drugs, such as etanercept, infliximab, or adalimumab, are recommended for the treatment of autoimmune diseases, such as rheumatoid arthritis, ankylosing spondylitis or inflammatory bowel disease, but are reported to cause peripheral neuropathy. Antifungal drugs, such as itraconazole and voriconazole, are reported to increase the risk of peripheral neuropathy. A combination of itraconazole and bortezomide also causes peripheral neuropathy.

The pathophysiology underlying chemotherapy-induced peripheral neuropathy is complex and drug dependent. Until a clearer understanding of the same emerges, the treatment would continue to be for symptoms of the disease. Mohty et al. [1] studied pathogenesis of peripheral neuropathy of bortezomib and thalidomide, but accurate grading of drug-induced neuropathy in the two cases was still not possible. The causes and mechanisms of drug-induced peripheral neuropathies of various drugs in animal models have been reviewed by Diezi et al. [2]. While studies on various drugs in animal models throw some light on the origins of chemotherapy-induced peripheral neuropathy, further validation is needed. The pathophysiology of drugs belonging to taxanes, vinca alkaloids, thalidomide, and bortezomib has been reviewed by Addington and Freiner [3]. The authors concluded that, while anti-neoplastic features of these drugs were well studied, the neurotoxic side effects are possibly unrelated to the anti-neoplastic pathway and remain unclear.

Difficulty in the treatment of peripheral neuropathy is the quantification of the magnitude of symptoms since accurate evaluation of signs and symptoms is the first step in the administration of a treatment. Methods have been developed to distinguish between various clinical components of peripheral neuropathy to separate pain, numbness, and tingling, which are measured on a scale of 0 to 10. National Cancer Institute's Common Toxicity Criteria score is one of the protocols for the evaluation of peripheral neuropathy. Visual Analog Scale (VAS) Score provides a complete assessment of symptoms, signs, ability aspects, and electrophysiology of the patient. Nerve conduction studies and needle electromyography help identify neural structure, axonal degeneration or demyelination, and the severity of axonal damage to confirm the diagnosis of peripheral neuropathy. Similarly, the European Organisation for Research and Treatment of Cancer developed a questionnaire to assess the severity of neuropathy for self-evaluation by patients [4].

Chemotherapy induced peripheral neuropathy may develop as a result of nerve injury at various anatomic regions of the nerve depending on the specific drug, and result in sensory peripheral neuropathy, motor peripheral neuropathy, and autonomic nerve damage.

While the causes of peripheral neuropathy are not equivocally established, it has been hypothesized that the myeloma protein produced by the malignant plasma cells, damages the nerve cells, resulting in symptoms of neuropathy. Amyloidosis can also cause peripheral neuropathy. High levels of paraprotein can result in hyperviscosity of the blood causing sluggish blood flow, which could lead to symptoms of peripheral neuropathy. Peripheral nerves leaving the spinal cord may be damaged due to a fractured vertebra caused by myeloma bone disease.

While various therapies practiced today provide symptomatic relief from drug-induced peripheral neuropathy, they do not treat the underlying causes. It is believed that no single drug is likely to be effective for the treatment of all peripheral neuropathies, which are a result of multiple causes.

In view of the differences in the origin of peripheral neuropathy and symptomatic nature of the treatment, the results often vary. In a critical review by Majithia et al. [5], the success of various drugs in the treatment of chemotherapy-induced peripheral neuropathy and recommendations of the American Society of Clinical Oncology was assessed. In Majithia et al., gabapentinoids were concluded to be useful in individual cases, but were not found to yield statistically significant results over placebos. Topical baclofen, amitriptyline, and ketamine (BAK) offered limited toxicity, but there was insufficient evidence to recommend them.

The symptoms of drug-induced neuropathy depend on the drug used, the dosage, and the cumulative dose administered. Damage due to the administered drug may not manifest for two to three months and may vary in terms of symptoms and duration of appearance. Drug dose adjustment during treatment is often used to ameliorate neuropathic pain. A wide range of drugs (such as gabapentin, pregabalin, tricyclic antidepressants, serotonin, norepinephrine reuptake inhibitors, carbamazepine, and opioid-type analgesics) are prescribed depending on the severity of symptoms, but with limited success.

Use of pregabalin 150-600 mg/d for at least 3 months or gabapentin 300-2,400 mg/d, duloxetine (30-60 mg/d) for the treatment of multiple myeloma induced peripheral neuropathy has been prescribed in the literature [1]. Recently, Mount Desert Island (MDI) Biological Laboratory has filed in 2016 a provisional patent, which mentions two new molecules that prevent paclitaxel-induced neurotoxicity by reducing the activity of MMP-13, (matrix-metalloproteinase 13). The two molecules prevented the degeneration of axons and restored the touch response in zebrafish. The molecules therefore have potential to reverse peripheral neuropathy, caused by various types of cancers as well as diabetes.

Researchers at the Catalan Institute of Oncology have reported a new molecule which would prevent the development of drug-induced peripheral neuropathy in cancer patients [6].

The 2018 global market for pain-relieving drugs is estimated at $10 billion. Chemotherapy-induced peripheral neuropathy (CIPN) affects 30% to 40% of patients treated and which is mainly symptomatic. The treatment includes administration of anticonvulsants, antidepressants, and opioids.

In view of the limited success and unpredictable performance of conventional drugs, a number of alternative treatments are being practiced for ameliorating the pain caused by the peripheral neuropathy. Complementary medicine is extensively practiced to the extent of 36% [7]. Capsaicin 0.075% gives a temporary analgesic effect. Lignocaine cream or patches produce a temporary local anaesthetic affect. Use of 1% topical menthol cream also leads to temporary improvements in pain and function.

Use of transcutaneous electrical nerve stimulation (TENS), low level light therapy (LLLT), or cold laser therapy and infrared light emitting diode (LED) therapy, acupuncture and reflexology are other methods suggested. Massage, yoga, and energy therapies have also been suggested.

Several supplements have also been suggested. These include amino acids Acetyl l-carnitine and glutamine, magnesium and Potassium supplements, fish and vegetable oils Omega-3 fatty acids, flaxseed oil, vitamin B complex that includes B1, B6, B12 and folic acid, vitamin E, alpha-lipoic acid, evening primrose oil, etc. It is recommended that these be supported by healthy and regular lifestyle, exercise, and relaxation techniques. However, use of supplements has been questioned in some publications [5].

In summary, chemotherapy-induced peripheral neuropathy is a problem associated with a wide range of drugs that needs to be addressed with ingenious solutions.

Vitamin K, especially vitamin K2-7, has been shown to be effective in various disease conditions, such as cardiovascular disease and osteoporosis.

Vitamin K is a family of structurally similar, fat-soluble, 2-methyl-1,4-naphthoquinones, including phylloquinone [vitamin K1] and menaquinones [vitamin K2]. The structural difference is in the substituent side chain at the gamma position. The other difference is in the activity and efficacy of these two isoforms, vitamin K1 and vitamin K2-7. A number of studies have shown that vitamin K1 has a half-life of 1.5 hours, whereas vitamin K2-7 has a half-life of more than 72 hours and is thus available to the body for a longer period with higher therapeutic activity. Vitamin K2-7 occurs in nature but is commercially produced by a range of bacteria also.

It has been observed that even at high doses, the natural forms of vitamin K2-7 have not produced symptoms of toxicity. Consuming more than the body's dietary needs for vitamin K does not cause any toxicity, especially related to blood clotting in healthy people.

Research in the field of vitamin K has resulted in novel applications. Traditionally, vitamin K has been associated with blood coagulation where it serves as a cofactor for the carboxylation of vitamin K-dependent proteins of coagulation cascade to render them active. It is now known that vitamin K is present in every tissue and by the virtue of its ubiquitous nature, the molecule plays an important role in bone mineralization, prevention of arterial calcification, apoptosis, phagocytosis, growth control, chemotaxis, and signal transduction. U.S. Pat. No. 8,354,129 claims food products to promote human bone health and cardiovascular health. U.S. Pat. No. 7,605,179 claims naphthoquinone-type compounds, including vitamin K, to modulate aggregation of protein associated with neurodegenerative diseases, such as Alzheimer's disease. The International Patent Application No. WO 2009/063485 discloses treatment of human disease conditions and disorders using vitamin K analogues and derivatives.

BRIEF DESCRIPTION OF THE DRAWING

The FIGURE is a visual analog scale (VAS) with gradations judged by a physician based on the following criteria. By using Visual Analog Scale, i.e. 0-10 point scale: 0=Absent; 1-3=Mild; 4-6=Moderate; 7-10=Severe.

DETAILED DESCRIPTION OF THE INVENTION

Vitamin K2-7 is now a well-established nutraceutical in the industry and its applications are well established. While developing newer applications of vitamin K2-7, it has now been surprisingly found that vitamin K2-7 ameliorates the symptoms of peripheral neuropathy caused by drugs used in the treatment of multiple myeloma.

The present invention relates to the therapeutic uses of vitamin K. It refers to compositions comprising vitamin K2-7 for the treatment of drug-induced neuropathy. More specifically, it refers to the compositions comprising vitamin K2-7 for the treatment of drug-induced peripheral neuropathy caused during the treatment of multiple myeloma.

Vitamin K2-7 compositions of the invention is in the form of capsule, tablets, syrups, and sachets.

In another embodiment of the invention, vitamin K2-7 compositions are used for treatment of peripheral neuropathy caused by drugs for the treatment of autoimmune diseases, such as etanercept, infliximab, leflunomide, azathioprine, cyclophosphamide, cyclosporine, mycophenolate, and methotrexate.

In one embodiment, the invention provides a vitamin K2-7 composition and use for treatment of peripheral neuropathy caused by anti-infectives, such as chloroquine, isoniazid, metronidazole, nitrofurantoin, and thalidomide.

In addition, the vitamin K2-7 composition is used for treatment of peripheral neuropathy caused by anti-cancer drugs, such as cisplatin, vincristine, and paclitaxel.

In another aspect of the invention, the vitamin K2-7 composition is used for treatment of peripheral neuropathy caused by anti-HIV drugs, such as didanosine, stavudine, and zalcitabine.

The invention also provides vitamin K2-7 composition for use in treatment of peripheral neuropathy caused by administration of drugs during the treatment of alcohol abuse, such as disulfiram.

In another aspect, the invention provides vitamin K2-7 compositions for use in the treatment of peripheral neuropathy caused by cardiovascular drugs, such as statins, especially simvastatin, pravastatin, fluvastatin, and amiodarone.

The vitamin K2-7 compositions are also used for treatment of peripheral neuropathy caused by drugs for the treatment of multiple myeloma, e.g. bortezomib and thalidomide. In another aspect, the vitamin K2-7 compositions are also used for treatment of peripheral neuropathy caused by drugs for the treatment of multiple myeloma, wherein the said drugs are selected from the group consisting of proteasome inhibitors (e.g. bortezomib), immune suppressants (e.g. cyclophosphamide), steroids (e.g. prednisolone), corticosteroids (e.g. dexamethasone), immune modulators (e.g. lenalidomide), bisphosphonates (e.g. zolendroic acid), monoclonal antibodies (e.g. rituximab), and vinca alkaloids (e.g. vincristine), or a combination thereof.

In another aspect of the invention, the vitamin K2-7 compositions are used for treatment of peripheral neuropathy caused by drugs lenalidomide and dexamethasone.

The invention also encompasses vitamin K2-7 compositions composition for use in the treatment of peripheral neuropathy caused by drugs lenalidomide and zolendroic acid or lenalidomide, dexamethasone, and zolendroic acid.

Furthermore, the invention provides vitamin K2-7 compositions for use in the treatment of peripheral neuropathy caused by drugs bortezomib, cyclophosphamide, and dexamethasone.

In an aspect of the invention, the composition comprises preferable 100 μg-700 μg of vitamin K2-7/day or more preferably 50 μg-1100 μg vitamin K2-7/day.

In an aspect of the invention, the composition of the invention is administered once or twice daily. It is envisaged that the vitamin K2-7 administered is released in the intestine.

In an aspect of the invention, the vitamin K2-7 composition of the invention is administered to a patient suffering from drug-induced peripheral neuropathy not cured by administration of vitamin B12.

In one aspect of the invention, the composition of the invention administered to a patient suffering from drug-induced peripheral neuropathy minimises or lowers the symptoms of drug-induced peripheral neuropathy.

In another aspect of the invention, the composition of the invention administered to a patient suffering from drug-induced peripheral neuropathy eliminates the symptoms of drug-induced peripheral neuropathy.

In yet another aspect of the invention, the composition of the invention administered to a patient simultaneously with the drugs that are reported to cause peripheral neuropathy minimises the symptoms of drug-induced peripheral neuropathy.

In an aspect of the invention, the composition of the invention administered to a patient simultaneously with the drugs that are reported to cause peripheral neuropathy prevents the occurrence of the symptoms of drug-induced peripheral neuropathy.

In an aspect of the invention, the composition of the invention administered to a patient simultaneously with the drugs that are reported to cause peripheral neuropathy, enables continued administration of the drugs for the treatment of multiple myeloma by minimizing the symptoms of drug-induced neuropathy.

In an aspect of the invention, the composition of the invention administered to a patient prior to the administration of the drugs that are reported to cause peripheral neuropathy prevents the occurrence of the symptoms of drug-induced peripheral neuropathy.

In an aspect of the invention, the vitamin K2-7 composition of the invention administered to a patient prior to the administration of the drugs that are reported to cause peripheral neuropathy minimises the symptoms of drug-induced peripheral neuropathy.

In an aspect of the invention, the vitamin K2-7 composition of the invention is administered to patient 2-24 weeks prior to the administration of the drugs that are reported to cause the symptoms of drug-induced peripheral neuropathy.

The composition comprising vitamin K2-7 of the invention is used for the treatment of peripheral neuropathy, wherein upon administration of vitamin K2-7, the patient is relieved of the symptoms of peripheral neuropathy during the next cycle of administration of the drugs for the treatment of multiple myeloma. Hence, vitamin K2-7 is used as a preventive nutraceutical to prevent the occurrence of symptoms of drug-induced peripheral neuropathy.

The beneficial effects on administration of vitamin K2-7 to patients suffering from chemotherapy-induced peripheral neuropathy during the treatment of multiple myeloma are now described below with examples which are illustrative and should not be in anyway considered as limiting the scope of the invention.

Example 1

An open labelled study was conducted to evaluate the effect of vitamin K2-7 on drug-induced peripheral neuropathy. Patients who were diagnosed with multiple myeloma and are on chemotherapy treatment for the same, were assessed for the occurrence of symptoms of peripheral neuropathy and then selected. Patients were given 2 capsules of 100 mcg or 350 mcg of vitamin K2-7 along with the ongoing chemotherapy. The evaluation of symptoms of peripheral neuropathy (such as tingling, numbness, burning sensation, muscle cramps etc.) were assessed by VAS score (Schematic 1) from 0 to 10 (nil to unbearable). The scale has been used in various studies to measure the intensity and severity of various symptoms of neuropathy [8, 9].

It was observed that before the beginning of vitamin K2-7 therapy, the VAS score in all the patients was between the range of "8" and "9" for the symptoms of tingling, numbness and burning sensation. As the patients continued with the therapy, it was observed that the VAS score for all the symptoms decreased to between the range of "1" and "2". This decrease has happened over a period of 2 to 5 months, depending upon the individual cases treated. Further, no adverse events were noted during the vitamin K2-7 therapy. Hence, it can be concluded that vitamin K2-7 helps in relieving the symptoms of drug-induced peripheral neuropathy significantly and helps patient for better compliance to the chemotherapeutic agents. The examples given in Table 1, summarises the data for 11 patients who were on vitamin K2-7 therapy for drug-induced peripheral neuropathy due to treatment for multiple myeloma. In Table 1, treatment administered refer to the cyclical chemotherapy provided to the patients of multiple myeloma (MM). These cycles are normally of 3 weeks or 21 days period, based on the attending physician's assessment of the patient's condition and tolerance.

However, vitamin K2-7 was administered daily as two 100 mg capsules. If patient did not respond to the 200 mg dose of vitamin K2-7 for a period of 2 cycles, then they were administered 350 µg/day of vitamin K2-7.

Thus, out of 11 patients, 1 patient remained on 100 µg of vitamin K2-7, two times a day daily, with significant improvement in peripheral neuropathy.

Treatment with vitamin K2-7 of subjects continued even after their having reached VAS score of "2". Such continues treatment stabilised the VAS Score. Further, it was noticed that continuation of vitamin K2-7 during the subsequent cycles prevented the flair up of the symptoms of drug-induced peripheral neuropathy. It was also observed that in patients administered with vitamin K2-7, the compliance rate of the for chemotherapy were improved significantly.

The gradation was judged by Physician based on following criteria. By using Visual Analog Scale, i.e. 0-10 point scale: 0=Absent; 1-3=Mild; 4-6=Moderate; 7-10=Severe.

TABLE 1

Summary of 11 patients receiving Vitamin K2-7 therapy for Drug induced Peripheral Neuropathy due to treatment for Multiple myeloma

| Patient ID | Start of Treatment for MM | Treatment Administered* | Date and Dosage of Administration of Vitamin K2-7 | VAS Score before starting Vitamin K2-7 | Date | VAS Score |
|---|---|---|---|---|---|---|
| 1 | June 2014 | 1, 2, 3 | 16 Jun. 15 (350 µg) | 8 | 10 Dec. 15 | 2 |
| 2 | 2014 | 4, 3 | 25 Jun. 15 (350 µg) | 8 | 05 Nov. 15 | 2 |
| 3 | 2015 | 4, 3, 5 | 19 Aug. 15 (100 µg) | 8 | 14 Mar. 16 | 2 |
| 4 | 2015 | 1, 2, 3 | 09 Jun. 16 (350 µg) | 8 | 22 Dec. 16 | 1 |
| 5 | 2016 | 1, 2, 3 | 23 Feb. 17 (350 µg) | 9 | 12 Aug. 17 | 2 |
| 6 | November 2014 | 6, 2, 7, 8, 9 | 22 May 17 (350 µg) | 9 | 04 Oct. 17 | 2 |
| 7 | 2010 | 4, 3 | 30 Jun. 17 (350 µg) | 8 | 27 Dec. 17 | 2 |
| 8 | March 2017 | 1, 2, 3 | 03 Nov. 17 (350 µg) | 7 | 03 Apr. 18 | 2 |
| 9 | 2016 | 1, 2, 3 | 20 Jul. 16 (350 µg) | 9 | 11 Jan. 17 | 2 |
| 10 | 2016 | 4, 3 | 10 Jun. 17 (350 µg) | 8 | 10 Jan. 18 | 3 |
| 11 | 2016 | 3 | 25 Mar. 17 (350 µg) | 9 | 29 Sep. 17 | 2 |

*1-Bortezomib, 2-Cyclophosphamide, 3-Dexamethasone, 4-Lenalidomide, 5-Zolendronic Acid, 6-Rituximab, 7- Doxorubicin, 8-Vincristine, 9-Prednisolone

REFERENCES

1. Bilal Mohty, Jean El-Cheikh, Ibrahim Yakoub-Aghaet. al. Peripheral neuropathy and new treatments for multiple myeloma: background and practical recommendations. Haematologica February 2010 (95): 311-319.
2. Diezi Manuela, BuclinThierrya andKuntzerThierryc. Toxic and drug-induced peripheral neuropathies: updates on causes, mechanisms and management. CurrOpin Neurol. 2013 October; 26(5):481-8.
3. J Addington and M Freimer. Chemotherapy-induced peripheral neuropathy: an update on the current understanding. F1000Research 2016, 5(F1000 Faculty Rev): 1466.
4. Grammatico S, Cesini L and Petrucci M. Managing treatment-related peripheral neuropathy in patients with multiple myeloma. Blood and Lymphatic Cancer: Targets and Therapy 2016:6 37-47.
5. Majithia N, Loprinzi C L and Smith T J. New Practical Approaches to Chemotherapy-Induced Neuropathic Pain: Prevention, Assessment, and Treatment. Oncology (Williston Park). 2016 Nov. 15; 30(11):1020-9.
6. Bruna, J., Videla, S., Argyriou, A. A. et. al. Efficacy of a Novel Sigma-1 Receptor Antagonist for Oxaliplatin-Induced Neuropathy: A Randomized, Double-Blind, Placebo-Controlled Phase IIa Clinical Trial. Neurotherapeutics (2018) 15: 178.
7. Idan Ben-Horin, Peretz Kahan and Larisa Ryvo. Acupuncture and Reflexology for Chemotherapy-Induced Peripheral Neuropathy in Breast Cancer. Integrative Cancer Therapies. 2017, Vol. 16(3) 258-262.
8. Wewers M E, Lowe N K. A critical review of visual analogue scales in the measurement of clinical phenomena. Res. Nur. Health 1990 August; 13(4):227-36.
9. Lakhan S E, Velasco D N and Tepper D. Botulinum Toxin-A for Painful Diabetic Neuropathy: A Meta-Analysis. Pain Mcd. 2015 September; 16(9):1773-80.

We claim:

1. A method of treating or ameliorating a symptom of cancer drug-induced peripheral neuropathy in a patient suffering from multiple myeloma, the method comprising administering a composition consisting essentially of vitamin K2-7 to the patient, wherein the peripheral neuropathy is caused by the cancer drug used in the treatment of multiple myeloma and the vitamin K2-7 is effective in treating or ameliorating at least one symptom of cancer drug-induced peripheral neuropathy.

2. The method of claim 1, wherein the cancer drug used in the treatment of multiple myeloma is selected from the group consisting of a proteasome inhibitor, an immune suppressant, a steroid, a corticosteroid, an immune modulator, a bisphosphonate, a monoclonal antibody, a vinca alkaloid, and combinations thereof.

3. The method of claim 2, wherein the proteasome inhibitor is Bortezomib.

4. The method of claim 2, wherein the immune suppressant is Cyclophosphamide.

5. The method of claim 2, wherein the steroid is Prednisolone.

6. The method of claim 2, wherein the corticosteroid is Dexamethasone.

7. The method of claim 2, wherein the immune modulator is lenalidomide.

8. The method of claim 2, wherein the bisphosphonate is zoledronic acid.

9. The method of claim 2, wherein the monoclonal antibody is Rituximab.

10. The method of claim 2, wherein the vinca alkaloid is vincristine.

11. The method of claim 1, wherein the dose of vitamin K2-7 is in the range of 50 µg/day to 1100 µg/day.

12. The method of claim 1, wherein the duration for lowering the symptoms of the drug induced peripheral neuropathy from severe to mild is in the range 2-5 months.

13. A method of preventing the symptoms of cancer drug-induced peripheral neuropathy in a patient suffering from multiple myeloma, the method comprising administering vitamin K2-7 to the patient, wherein the peripheral neuropathy is caused by the cancer drug used in the treatment of multiple myeloma and the vitamin K2-7 is effective in treating or ameliorating at least one symptom of cancer drug-induced peripheral neuropathy.

* * * * *